United States Patent [19]
Upmeyer et al.

[11] Patent Number: 5,834,004
[45] Date of Patent: Nov. 10, 1998

[54] ENTERAL COMPOSITION COMPRISING DIMETHICONE AND A PHOTOSENSITIZER AND A METHOD OF DELIVERY

[76] Inventors: Hans-Jürgen Upmeyer, Mauerkircherstrasse 197, 81925 München; Alfred Schmidt, Leinpfad 2, 22301 Hamburg, both of Germany

[21] Appl. No.: 716,161

[22] PCT Filed: Mar. 15, 1995

[86] PCT No.: PCT/EP95/00973

§ 371 Date: Jan. 21, 1997

§ 102(e) Date: Jan. 21, 1997

[87] PCT Pub. No.: WO95/25545

PCT Pub. Date: Sep. 28, 1995

[30] Foreign Application Priority Data

Mar. 18, 1994 [DE] Germany .......................... 44 09 410.8

[51] Int. Cl.⁶ .................................................. A61K 47/34
[52] U.S. Cl. ........................................ 424/423; 514/772.1
[58] Field of Search .............................. 514/772.1, 772.3; 424/423

[56] References Cited

U.S. PATENT DOCUMENTS

| | | |
|---|---|---|
| 4,837,029 | 6/1989 | Olsen . |
| 4,960,764 | 10/1990 | Figueroa, Jr. et al. . |
| 5,229,137 | 7/1993 | Wolfe . |
| 5,422,093 | 6/1995 | Kennedy et al. . |

FOREIGN PATENT DOCUMENTS

| | | |
|---|---|---|
| 219076 | 4/1987 | European Pat. Off. . |
| 428296 | 5/1991 | European Pat. Off. . |
| M3848 | 1/1966 | France . |
| 2 110314 | 6/1972 | France . |
| 3 642853 | 6/1988 | Germany . |
| 3 807712 | 2/1989 | Germany . |
| 90 07930 | 7/1990 | WIPO . |
| 91 04034 | 4/1991 | WIPO . |
| 94 03209 | 2/1994 | WIPO . |
| 95 05813 | 3/1995 | WIPO . |

OTHER PUBLICATIONS

Bioforum May 1993, p. 189.
Rote Liste 1993, pp. 289 and 299.
Marshall, B.J.: Unidentified Curved Bacilli on Gastric Epithelium in Active Chronic Gastritis; Lancet I (1983), pp. 1273–1275.
Dixon, M.F.: Helicobacter Pylori and Peptic Ulceration: Histopathological Aspects (1991), pp. 125–130.

*Primary Examiner*—Edward J. Webman
*Attorney, Agent, or Firm*—Birch, Stewart, Kolasch & Birch, LLP

[57] ABSTRACT

The invention relates to dimethylpolysiloxane (dimethicone) to be used as a transport and carrier system and/or a drug delivery system for pharmaceutical drugs. Moreover, the invention relates to pharmaceutical compositions containing dimethylpolysiloxane as a transport and carrier system and/or as a drug delivery system in combination with an active ingredient such as photosensitizer, e.g., δ-amino levulinic acid.

7 Claims, No Drawings

ENTERAL COMPOSITION COMPRISING DIMETHICONE AND A PHOTOSENSITIZER AND A METHOD OF DELIVERY

TECHNICAL FIELD OF THE INVENTION

This application is a continuation under 35 U.S.C. 371 of PCT/EP95/00973, filed Mar. 15, 1995.

The invention relates to dimethylpolysiloxane (dimethicone) to be used as a transport and carrier system and/or a drug delivery system for pharmaceutical drugs for instance for the treatment of gastro-intestinal diseases. Moreover, the invention relates to pharmaceutical compositions containing dimethylpolysiloxane as a transport and carrier system and/or as a drug delivery system in combination with an active ingredient and methods related thereto.

Commercial dimethicone-containing preparations are used to treat symptoms such as flatulence, sensation of repletion (bloating) and meteorism. Moreover, the use of dimeticone for treating inflammatory and ulcerous diseases of the esophagus, the stomach and the duodenum has been described.

BACKGROUND OF THE INVENTION

In order to avoid dose-related side effects, the galenics of a pharmaceutical composition should be such that only the dose of the active ingredient necessary to elicit the desired therapeutic effect needs to be administered.

Hence, it is desirable to apply the therapeutically active ingredient right at the site where it is to produce its effect or at the site where it is absorbed so as to increase the local bioavailability and/or general bioavailability of the active ingredient (for instance by averting a first pass effect in the liver) or so as to avoid systemic side effects as much as possible.

In view of the different physiological properties of the different sections of the gastro-intestinal tract (GI tract), local therapy is particularly difficult in this case.

The continuous peristalsis, the variation of the chemical conditions over the length of the digestive tract, and the morphology of the surface of the GI tract are obstacles to a prolonged residence time in the different sections of the tract (such as the esophagus, stomach, duodenum, and colon).

Especially in the case of chronic diseases, such as inflammatory, infectious, ulcerous or neoplastic changes of the GI tract, direct local therapy capable of being continued over a prolonged period of time is desirable.

Furthermore, local treatment is also desirable in the case of disorders in the cardiovascular system, the lungs, the brain, and all hollow organs.

Local treatment requires a suitable transport and carrier system and/or drug delivery system.

SUMMARY OF THE INVENTION

The present invention provides a carrier that lends itself for use in particular galenic pharmaceutical forms for oral, rectal and intraoperative applications which release and/or fix the active ingredient continuously at the very site where it is to produce its effect or is absorbed.

It was surprisingly found that dimethicone, because of its unique physico-chemical properties is ideally suited for such purposes. Dimethicone has a very wide range of viscosities, depending on the degree of polymerization. The viscosity of dimethicone to be used in accordance with the invention may vary, depending on the therapeutical purpose, the nature and location of the condition to be treated as well as the drug to be administered. Preferably, dimethicone having a kinematic viscosity in the range of 10 to 100,000 $mm^{2\cdot} S^{-1}$ is used.

The use of dimethicone having a kinematic viscosity in the range of 300 to 1,500 $mm2.5 S^{-1}$ is particularly preferred. Dimethicone may also be supplemented with silicone dioxide as it is for example contained in the product Simeticone.

Dimethicone was found to show a particular association with or affinity to the surface structure of the GI tract. Because of an increased adhesion resulting from the adhesive properties of dimethicone, the residence time of an active ingredient in a region of the GI tract can be substantially prolonged if dimethicone is used as a transport or carrier system.

However, because of the different chemical, morphological and physiological conditions along the GI tract, the affinity and association of dimethicone with the epithelial cells of the GI tract is not uniform. Thus, in order to optimize the effect of dimethicone as a transport and carrier system and/or drug delivery system for any particular drug at any particular site of the GI tract, dimethicone with the appropriate viscosity should be chosen, depending on the nature of the therapy and drug as well as the location in the GI tract. This may readily be determined by experimentation.

The use of dimethicone is not limited to the treatment of the GI tract. It may also be used in the treatment of the cardiovascular system the lungs, the brain and all hollow organs.

According to the invention, dimethicone was found to be particularly suitable as a transport and carrier system or a drug delivery system for cytostatic drugs, immunosuppressants, immunomodulating and immunostimulative substances, biological response modifying (BRM) substances, radio-, chemo- and photosensitizers, anti-inflammatory substances, such as corticoids, antibiotics, analgesics, locally effective anestetics, antiphlogistics, non-steroidal antirheumatics, antiviral substances, bismuth preparations and motility inhibiting and motility enhancing substances.

The function of dimethicone as a carrier for the photosensitizer δ-amino levulinic acid (ALA), the $H_2$ antagonists (such as ranitidine and cimetidine) and the proton pump inhibitors (such as omeprazole and lansoprazole) is particularly preferred.

The pharmaceutical compositions which contain dimethicone in combination with one of the. afore-mentioned substances therefore lend themselves particularly well for the treatment of inflammatory, infectious, ulcerous and neoplastic diseases of the GI tract.

In the treatment of disorders in the lower area of the GI tract, the dimethicone-containing pharmaceutical composition may be formulated in an enteral form according to conventional methods in order to prevent dimethicone and the active ingredient from remaining in the upper zone of the GI tract. Alternatively, the properties of the pharmaceutical composition should be so adjusted that it has an increased affinity for the lower part of the GI tract.

Direct application, for instance via the bioptic channel of an endoscope, bronchoscope or proctoscope, intraoperative or by instillation, is particularly preferred.

The dimethicone-containing pharmaceutical composition should also contain highly dispersed silicon dioxide and/or a pharmaceutically acceptable surface-active agent.

The ratio of dimethylpolysiloxane to the surface-active agent is preferably 3 to 10:1, in particular 4 to 6:1, and the ratio of highly dispersed silicon dioxide to dimethylpolysiloxane is preferably 3 to 50% (wt/wt). A preferred range for the latter ratio is 30 to 40% (wt/wt), the value of 35 to 36% being particularly preferred.

The concentration of the surface active agent is preferably at least 1.5% (wt/wt). A particularly preferred dimethicone formulation contains 8–10% (wt/wt) of the surface active agent.

Stearic salts or long chain alkanoic acids, in particular $C_{11}$–$C_{18}$ alkanoic acids, such as myristic acid, palmitic acid and stearic acid, and their salts, such as magnesium or calcium salts and mixtures thereof can be suitably used as pharmaceutically acceptable surface active agents.

The invention is illustrated by the following example.

EXAMPLE

| δ-amino levulinic acid containing emulsion (ALA) | |
|---|---|
| | amount/dose mg/250 ml |
| ALA | 5,000.0000 |
| simeticone | 2,000.0000 |
| (dimethicone 1000 - $SiO_2$ 94:6) | |
| Aerosil 200 | 125.0000 |
| Kollidon CL M[1] | 2,500.0000 |
| hydroxyethylcellulose | 20,000.0000 |
| Veegum K[2] | 2,500.0000 |
| cinnamon oil DA B 10 | 0.1228 |
| 85% indigotin | 0.0250 |
| water, purified | ad 250 ml |

[1]= polyvinylpyrrolidone (INN: providone)
[2]= colloidal magnesium = aluminum silicate The emulsion of the Example is intended for the photodynamic therapy of tumors of the GI tract, the emulsion being applied by means of an endoscope at the very site where the effect is to be elicited.

While we have described an embodiment of this invention, it is apparent that our embodiment may be altered to provide other embodiments which utilize the method of this invention. Therefore, it will be appreciated that the scope of this invention is to be defined by the appended claims, rather than by the specific embodiment which has been presented by way of example.

We claim:

1. A pharmaceutical composition for enteral administration comprising dimethylpolysiloxane in combination with a photosensitizer.

2. The pharmaceutical composition according to claim 1 wherein the photosensitizer is δ-amino levulinic acid (ALA).

3. The composition according to claim 1, wherein said dimethicone has a kinematic viscosity in the range of 10 to 100,000 $mm^2 \cdot s^{-1}$.

4. The composition according to claim 1, wherein said dimethicone has a kinematic viscosity in the range of 300 to 1,500 $mm^2 \cdot s^{-1}$.

5. The composition according to claim 1, wherein said composition further comprises silicone dioxide.

6. A method of increasing the residence time of a photosensitizer in the GI tract which comprises administering the composition according to claim 1 to said GI tract.

7. A method of increasing the residence time of a photosensitizer in the GI tract which comprises administering the composition according to claim 2 to said GI tract.

* * * * *